United States Patent [19]
Reinehr et al.

[11] 4,290,964
[45] Sep. 22, 1981

[54] UNDESCANOIC ACIDS AND ESTERS THEREOF

[75] Inventors: Dieter Reinehr, Kandern, Fed. Rep. of Germany; Paul Lienhard, Frenkendorf, Switzerland

[73] Assignee: Ciba-Geigy Corporation, Ardsley, N.Y.

[21] Appl. No.: 126,081

[22] Filed: Feb. 29, 1980

[30] Foreign Application Priority Data

Mar. 12, 1979 [CH] Switzerland .................. 2330/79

[51] Int. Cl.$^3$ ............................................. C09F 5/00
[52] U.S. Cl. .................................................. 260/404
[58] Field of Search .......................................... 260/404

[56] References Cited
U.S. PATENT DOCUMENTS

| | | | |
|---|---|---|---|
| 3,244,733 | 4/1966 | Wakasa | 260/404 |
| 3,554,755 | 1/1971 | Rinawro | 260/404 |
| 3,839,370 | 10/1974 | Henrick | 260/404 |
| 3,883,586 | 5/1975 | Yokoyama et al. | 260/404 |

OTHER PUBLICATIONS

McKay et al. "Amino Alcohols," Canadian Journal of Chemistry, vol. 36, p. 149 (1958).

*Primary Examiner*—John F. Niebling
*Attorney, Agent, or Firm*—Harry Falber

[57] ABSTRACT

The invention relates to 11-aminoundecanoic acids and 11-aminoundeca-4,8-dienoic acids and the esters of these acids. They have the formula I

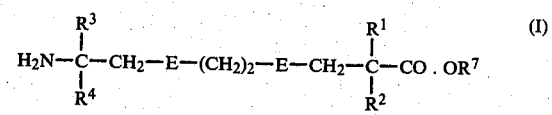

wherein $R^1$ and $R^3$ are e.g. hydrogen and $R^2$ and $R^4$ are e.g. methyl and E is e.g. the radical $-CH_2CH_2-$ and $R^7$ is hydrogen or an alkyl radical. The esters are suitable for the manufacture of salts of anionic dyes which are very readily soluble in organic solvents.

8 Claims, No Drawings

UNDESCANOIC ACIDS AND ESTERS THEREOF

The present invention relates to 11-aminoundecanoic acids and 11-aminoundeca-4,8-dienoic acids which are at least disubstituted in the carbon chain, the esters of these acids, and processes for obtaining these compounds. The compounds are novel and the esters are useful starting materials for the manufacture of high-grade azo dyestuff salts.

11-Aminoundecanols which are at least disubstituted in the carbon chain, and the production thereof, have been described in German Offenlegungsschrift No. 2 831 299. The unsubstituted 11-aminoundecanoic acid is described in "Lehrbuch der organischen Chemie", H. Beyer, S. Hirzel Verlag, Leipzig, 1968, page 345.

Known dye salts, for example the azo dyestuff alkali salts described in G.B. patent specification No. 1,296,857, have the drawback that their solubility in organic solvents is relatively limited.

It is the object of the present invention to provide aliphatic saturated and unsaturated aminocarboxylic acid esters which are suitable for the production of salts of anionic dyes, especially of azo dyestuff sulfonic acid salts, which have better solubility in organic solvents than the known salts of anionic dyes. It is a further object of the invention to provide the free acids of these esters which are starting materials for these latter.

Accordingly, the invention provides compounds of the formula I

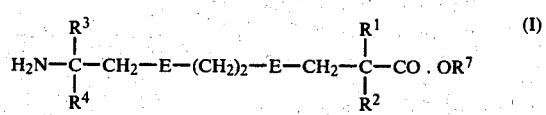

wherein each of $R^1$ and $R^3$ independently is hydrogen or a straight chain or branched alkyl radical of 1 to 8 carbon atoms, and $R^3$ is also a phenyl radical, $R^2$ is a straight chain or branched radical of 1 to 8 carbon atoms and $R^4$ is a straight chain or branched alkyl radical of 1 to 18 carbon atoms, or $R^1$ and $R^2$ and/or $R^3$ and $R^4$ together with the carbon atom to which they are attached form a cycloaliphatic ring containing 4 to 8 carbon atoms, and wherein each E represents one of the radicals $$\begin{array}{cc} R^5 & R^6 \\ | & | \\ -CH-CH- \end{array} \quad \text{and} \quad \begin{array}{cc} R^5 & R^6 \\ | & | \\ -C=C- \end{array}$$

in which each of $R^5$ and $R^6$ independently is hydrogen or alkyl of 1 to 4 carbon atoms and $R^7$ is hydrogen or a straight chain or branched alkyl radical containing altogether 1 to 18 carbon atoms.

Preferred compounds are 11-aminoundecanoic acids of the formula I wherein $R^7$ is hydrogen and E is the radical $$\begin{array}{cc} R^5 & R^6 \\ | & | \\ -CH-CH- \end{array}.$$

Especially interesting compounds are also 11-aminoundecanoates of the formula I, in which $R^7$ is a straight chain or branched alkyl radical containing altogether 1 to 18, preferably 1 to 8, carbon atoms, and E is the radical $$\begin{array}{cc} R^5 & R^6 \\ | & | \\ -CH-CH-; \end{array}$$

and 11-aminoundeca-4,8-dienates of the formula I, in which $R^7$ is also a straight chain or branched alkyl radical containing altogether 1 to 18, preferably 1 to 8, carbon atoms, and E is the radical $$\begin{array}{cc} R^5 & R^6 \\ | & | \\ -C=C- \end{array}.$$

A further preferred embodiment of the invention comprises compounds of the formula I, wherein each of $R^5$ and $R^6$ is hydrogen, each of $R^1$ and $R^3$ independently is hydrogen or alkyl of 1 to 5 carbon atom, $R^2$ is alkyl of 1 to 5 carbon atoms and $R^4$ is alkyl of 1 to 7 carbon atoms, or wherein each of $R^3$, $R^5$ and $R^6$ is hydrogen, $R^1$ and $R^2$ together with the carbon atom to which they are attached are cyclopentyl or cyclohexyl, and $R^4$ is alkyl of 1 to 7 carbon atoms.

Further preferred compounds are those of the formula I, wherein each of $R^3$, $R^5$ and $R^6$ is hydrogen, each of $R^1$ and $R^2$ independently is alkyl of 1 to 4 carbon atoms or together with the carbon atom to which they are attached are cyclohexyl, and $R^4$ is alkyl of 1 to 7 carbon atoms. Preferred compounds are also those of the formula I, wherein $R^3$ is hydrogen and $R^4$ is the radical

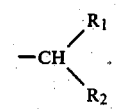

Especially preferred is a compound of the formula I, wherein each of $R^1$ and $R^2$ is —$CH_3$, $R^3$ is hydrogen, $R^4$ is —$CH(CH_3)_2$, E is —$CH_2CH_2$— and $R^7$ is n-pentyl.

The compounds of the formula (I) are obtained by reacting a 1-azacyclododecene of the formula (II)

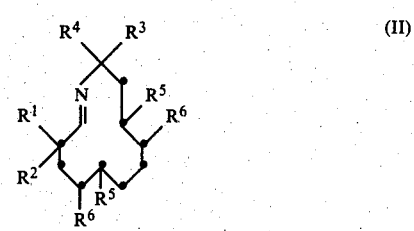

or a 1-aza-1,5,9-cyclododecatriene of the formula III

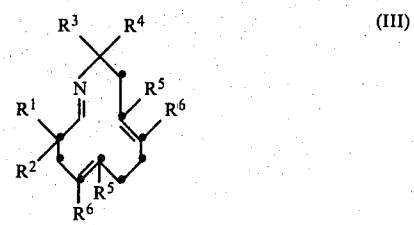

in aqueous or aqueous-organic medium, in the presence of an inorganic acid, by methods known per se, to produce compounds of the formula

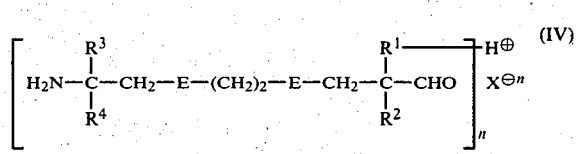

in which formulae (II) to (IV), $R_1$ to $R_6$ and E are as defined for formula (I), X is the anion of the inorganic acid and n is an integer corresponding to the valency of X, and subsequently oxidising the compounds of the formula (IV) to the respective 11-amino-undecanoic acids or 11-amino-undeca-4,8-dienoic acids of the formula I, and, optionally, in a third reaction step, reacting these acids by known methods with an alcohol of the formula $R^7OH$, wherein $R^7$ represents a straight chain or branched alkyl radical of altogether 1 to 18 carbon atoms, to produce the corresponding esters of the formula (I).

If in the above process the starting material employed is a 1-azacyclododecene of the formula II, the products obtained are the corresponding 11-aminoundecanoic acid and the ester thereof. If, on the other hand, the starting material is a 1-aza-1,5,9-cyclododecatriene of the formula III, the products obtained are the corresponding 11-aminoundeca-4,8-dienoic acids and the esters thereof. Both the 11-aminoundeca-4,8-dienoic acids and their esters are obtained in the form of mixtures of isomers.

The hydrolysis of the compounds of the formulae II or III is carried out in the first step of the process in exact analogy to the procedure described in German Offenlegungsschrift No. 2 831 299. It is carried out in the presence of an inorganic acid in aqueous or aqueousorganic medium.

Examples of suitable organic solvents are alcohols, especially those containing 1 to 4 carbon atoms, aliphatic diols, e.g. 1,2-ethanediol, 1,3-propanediol and 1,4-butanediol, and cyclic ethers, e.g. tetrahydrofurane and dioxane. It is preferred to carry out the hydrolysis in aqueous medium.

As inorganic acids it is possible to use e.g. hydrohalic acids such as HCl and HBr, sulfuric acid, phosphoric acid, dilute nitric acid and perchloric acid. It is preferred to carry out the hydrolysis in the presence of sulfuric acid.

The hydrolysis is carried out as a rule in the temperature range from about 0° to 60° C., with the preferred range being from about 20° to 40° C. The salts of the formula IV obtained after the hydrolysis can be isolated, if desired, in a manner known per se, e.g. by concentrating the reaction mixture. However, such an isolation is usually not necessary.

Before the oxidation step, however, the reaction mixture is usually treated for 15 minutes with steam in order to remove aldehyde and other volatile impurities. The second step of the oxidation is preferably carried out by stirring the reaction mixture in the temperature range between 0° and 200° C., preferably between 20° and 100° C., under a pressure between 1 and 100 bar, preferably between 3 and 20 bar, in an atmosphere of oxygen or oxygen-containing gases. The process can also be carried out in the presence of transition metal salts, e.g. iron, nickel, copper, chromium, cobalt and manganese salts, which help catalyse the oxidation. Specific examples of such salts are: iron(II), iron(III), cobalt(II), cobalt(III), nickel(II), manganese(II), copper(I) and copper(II) salts of inorganic or organic acids, such as HCl, $H_2SO_4$ and acetic acid. The corresponding readily soluble acetates, 2-ethylhexanoates, acetylacetonates, phenolates and stearates are very suitable.

The reaction mixture obtained is preferably neutralised with sodium hydroxide solution, whereupon the respective 11-aminoundecanoic acid precipitates in the form of a relatively pure product. It will be understood that the 11-aminoundecanoic acid can be further purified by known methods by recrystallisation e.g. from alcohol/water mixtures. If an ester of the formula I is obtained therefrom, it is usually possible to use the initially precipitated acid, which, if desired, is washed with water, without further purification operations.

If the product obtained after neutralising the reaction mixture of the oxidation step is a 11-aminoundeca-4,8-dienoic acid, then this latter is usually obtained as a mixture of isomers in the form of an oily precipitate.

The original reaction mixture obtained after the oxidation step can usually also be re-used direct, without separation and purification of the acid, for the production of the 11-aminoundeca-4,8-dienates of the invention.

The 11-aminoundecanoic and 11-aminoundeca-4,8-dienoic acids can also be purified by first dissolving the crude product by addition of an aqueous acid or base and then extracting the resultant aqueous solution with an ether, such as diethyl ether. After this purification, the amino acid can again be precipitated from the aqueous solution by neutralisation.

The esterification of the 11-aminoundecanoic or 11-aminoundeca-4,8-dienoic acid with alcohols of the formula $R^7\text{-}OH$ is carried out by methods known per se in the presence of an inorganic acid, preferably sulfuric acid.

In the manufacture of the preferred compounds of the formula I individually referred to above, there are used the respective suitable starting materials of the formulae II and III and, optionally, of the formula $R^7\text{-}OH$, wherein $R^1$ to $R^7$ and E have the same meanings as in the compounds of the formula I which it is particularly desired to obtain.

The manufacture of the starting materials of the formula III has already been described in detail in, inter alia, German Offenlegungsschrift No. 2 831 299. It is also carried out as described in Helv. Chim. Acta, 61, fascicle 3, 1122–1124 (1978), by nickel-catalysed co-oligomerisation of 2-aza-1,3-butadienes of the formula V

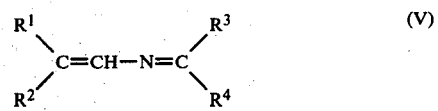

with compounds of the formula VI

wherein $R^1$ to $R^6$ are as defined for formula I. Suitable catalyst systems are described e.g. in German Offenlegungsschrift No. 2 330 087. Preferred catalysts are those which are obtained in situ by reduction of a carbon monoxide-free nickel compound, such as nickel stearate and, especially, nickel acetylacetonate, with halogen-free metal aryls or metal alkyls, e.g. ethoxy diethyl aluminium, in the presence of an alkyl or aryl phosphine or of an alkyl or aryl phosphite.

The above reaction is advantageously carried out in the presence of an inert organic solvent, such as n-hexane, n-heptane, benzene, toluene, diethyl ether or dioxane, in the temperature range between about $-40°$ and $+150°$ C.

Most of the 2-aza-1,3-butadienes of the formula V are known or they can prepared e.g. as follows:

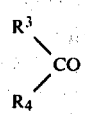

by reaction of aldehydes $R^3$-CHO or ketones with alkenylamines $H_2N\text{-}CH_2\text{-}C(R^{1'})\!=\!CH\text{-}R^{2'}$ [$R^{1'}=$hydrogen or $C_1\text{-}C_8$alkyl, $R^{2'}=$hydrogen or $C_1\text{-}C_7$alkyl] and subsequent isomerisation of the resultant compounds $R^{2'}\!-\!CH\!=\!C(R^{1'})\text{-}CH_2\text{-}N\!=\!C(R^3)(R^4)$ in the presence of catalysts, such as $K_2O/Al_2O_3$ catalysts, alkali metal alcoholates or alkaline earth metal alcoholates [cf. for example B. A. Kazanskii et al., Zhurnal Organicheskoi Khimii, 6, No. 11,2197–99 (1970; Izw. Akad. Nauk SSSR, Ser. Khim., No. 9,2038–2045 (1975) and Tetrahedron, 34, 833–839 (1978)];

by reaction of allylamine or methallylamine with aldehydes $(R^1)(R^{2''})$-CH-CHO [$R^{2''}$ has the same meaning as $R^2$ but not hydrogen] and subsequent isomerisation of the resultant compounds $(R^1)(R^{2''})$-CH-CH$=$N-CH$_2$-C(R)$=$CH$_2$ [R = hydrogen or methyl] in the presence of catalysts, such as potassium tert-butylate;

by reaction of aldehydes $R^1$-CH($R^{2''}$)-CHO [$R^{2''}$ has the same meaning as $R^2$ but not hydrogen] with ammonia (cf. for example U.S. Pat. No. 2,319,848) and possible further reaction of the resultant compounds $(R^1)(R^{2''})$-C$=$CH-N$=$CH-CH($R^{2''}$)($R^1$) with suitable ketones or aldehydes (cf. for example U.S. Pat. No. 3,706,802).

The starting materials of the formula II can be prepared by catalytic hydrogenation of the 1-aza-1,5,9-cyclododecatrienes of the formula III by methods known per se. This hydrogenation is advantageously carried out in the presence of suitable inert solvents and normally in closed systems at a pressure of about 1 to 200 bar, especially 1 to 130 bar. The hydrogenation temperature is as a rule in the range between about 0° and 150° C., especially between about 25° and 100° C.

The preferred catalysts are rhodium/aluminium oxide or palladium on carbon catalysts.

The 11-aminoundecanoates and 11-aminoundeca-4,8-dienates of the present invention are starting materials for the manufacture of anionic dyes which are especially readily soluble in organic solvents, preferably anionic azo dyes. Using the esters of the invention it is possible in particular to obtain the very valuable azo dyestuff sulfonic acid salts of the formula VII

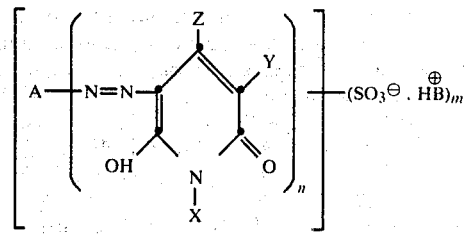

or of a tautomer thereof, wherein A is a carbocyclic or heterocyclic aromatic radical, B is the respective 11-aminoundecanoate or 11-aminoundeca-4,8-dienate of the formula I, X is a hydrogen atom or a substituted or unsubstituted alkyl group, a cycloalkyl, aralkyl or aryl group, Y is a hydrogen or halogen atom or an electrophilic group, for example a nitro, cyano, acyl, sulfonic acid, arylsulfonyl, alkoxycarbonyl group or a substituted or unsubstituted alkyl, sulfamoyl or carbamoyl group, Z is a substituted or unsubstituted alkyl group or an aryl radical, and m and n are 1 or 2.

If n is 1, A is a monovalent, preferably carbocyclic, aromatic radical, for example a naphthalene radical, but is in particular an unsubstituted or a substituted phenyl radical. If n is 2, A is a divalent radical, preferably a diphenyl, diphenyl ether or diphenylsulfonyl radical. An alkyl group X is preferably a $C_1$–$C_{18}$ alkyl group which can be substituted, for example by hydroxyl groups, alkoxy groups of 1 to 8 carbon atoms or by phenyl groups which are unsubstituted or substituted by chlorine, methyl or $-SO_3H$. If n is 1, the alkyl group can also be a radical of the formula $$\left( A\text{-}N\!=\!N\!-\!\underset{HO}{\overset{Z}{\diagdown}}\!\!\!\!\!\underset{N}{\overset{Y}{\diagup}}\!\!\!\!\!\overset{}{\underset{}{O}} \right)\!-\!(SO_3 \cdot HB)_m$$

A cycloalkyl group X is in particular cyclohexyl. An aralkyl group X is in particular a phenylalkyl group containing 1 to 4 carbon atoms in the alkyl moiety. An aryl group X is preferably phenyl which is unsubstituted or substituted by chlorine, methyl or $-SO_3H$. An alkyl group Y is preferably a $C_1$–$C_6$ alkyl group which can be substituted for example by a sulfonic acid group or an alkanoylamino group of 2 to 7 carbon atoms. An acyl group Y is preferably an alkanoyl group of 2 to 7 carbon atoms or a benzoyl group. Carbamoyl or sulfamoyl represented by Y can be unsubstituted or substituted by one or two $C_1$–$C_6$alkyl groups or a phenyl radical which is unsubstituted or substituted by chlorine atoms or methyl groups. An alkoxycarbonyl group Y preferably contains 2 to 7 carbon atoms. As an arylsulfonyl group, Y is preferably a phenylsulfonyl group. An alkyl group Z preferably contains 1 to 6 carbon atoms and can be substituted by a sulfonic acid group or a phenyl radical. As an aryl radical, Z is preferably a phenyl radical which can be substituted by chlorine, methyl or $C_1$–$C_6$ alkoxy.

The dyes salts are obtained by reacting the corresponding azo dyestuff monosulfonic or disulfonic acid with 1 or 2 moles respectively of the amino ester B.

The azo dyestuff sulfonic acids are known compounds which are described e.g. in the following publications: German Offenlegungsschriften Nos.: 1 924 570, 2 004 487, 2 050 901, 2 134 453, 2 150 817, 2 237 006, 2 533 723, 1 930 491, 2 004 488, 2 115 449, 2 141 449, 2 162 612, 2 238 795, 2 545 828, 1 956 142, 2 033 281, 2 123 061, 2 141 453, 2 216 206, 2 349 709, 2 701 290, British patent specification Nos.: 1,296,857, 1,331,261, 1,345,864.

The azo dyestuff sulfonic acids are obtained by coupling a diazotised or tetraazotised carbocyclic or heterocyclic aromatic amine with a pyridone of the formula

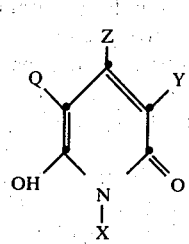

or of a tautomer thereof, wherein Q represents a hydrogen atom or an easily removable radical, for example the carbamoyl group, and X, Y and Z have the given meanings, the components being so chosen that the resultant azo dye contains at least one sulfonic acid group.

The salt formation is advantageously carried out by reacting a solution or suspension of an alkali metal salt of the dyestuff sulfonic acid with the aqueous solution of a water-soluble salt of the respective 11-aminoundecanoate or 11-aminoundeca-4,8-dienate, preferably one with a lower fatty acid, in particular formic acid or acetic acid. It is advantageous to carry out this reaction in the temperature range between 40° and 80° C. and at a pH value below 7.

As the dye salts are insoluble in the aqueous reaction medium, they can be isolated by filtration.

The reaction can also be carried out, however, in organic solvents alone or in mixtures thereof with water.

The dye salts have excellent solubility in alcohols, especially in lower alkanols, such as methanol, ethanol, n-propanol or isopropanol, in alkylene glycol monoalkyl ethers, for example in ethylene glycol monomethyl or monoethyl ether, in alkylene glycols, for example in propylene glycols, or in aralphatic alcohols, for example in benzyl alcohol, or in mixtures of such alcohols, in lower aliphatic ketones, for example acetone, methyl ethyl ketone, methyl isobutyl ketone or also in cyclohexanone, in carboxylic acid esters, for example methyl acetate, ethyl acetate, butyl acetate or glycol monoacetate, and also in halogenated hydrocarbons, preferably lower aliphatic hydrocarbons, such as chloroform, methylene chloride, ethylene chloride or carbon tetrachloride.

Because of their good solubility, the dye salts of the present invention are suitable for the spin-dyeing of cellulose 2½-acetate; and because of their good solubility in halogenated lower aliphatic hydrocarbons, especially chloroform, and methylene chloride/methanol (9:1), they can also be used for the spin dyeing of cellulose triacetate. The spin-dyed fabric is distinguished by purity and depth of shade, by excellent distribution of the colourant, and by very good fastness properties, such as fastness to washing, water, bleaching, cross-dyeing, dry-cleaning, rubbing, ironing, dry heat and light.

On account of their good solubility in alcohols, esters and mixtures thereof, the dye salts of the invention are particularly suitable for colouring film-forming polymers.

By alcoholic and/or ester-containing solutions of film-forming polymers are meant in this context in particular those liquid vehicles which are suitable for use in printing inks for flexographic printing. As polymers, these solutions contain, for example, neutral resins such as shellac or Manila copal, or cellulose derivatives, for example cellulose ethers, such as ethylcellulose or cellulose esters, such as nitrocellulose; and also maleate resins or phenol-formaldehyde resins, polyamide resins, urea-formaldehyde and melamine-formaldehyde condensation products, ketone-formaldehyde condensation products, polyvinyl acetates or polyacrylic acid resins, for example polybutyl acrylate resin, or their mixtures; polycondensation products of polyvalent alcohols, such as glycerol or pentaerythritol, with polybasic acids, such as maleic acid or phthalic acid alone or in combination with unsaturated fatty acids, such as those of linseed oil and castor oil.

These solutions of film-forming polymers containing the above dye salts are suitable e.g. for printing a variety of materials, such as metal foils, for example aluminium foils, paper, glass, synthetic resin sheets and films and the like. They are also suitable for coating a wide variety of surfaces, e.g. metal parts, plastic mouldings or wooden boards. They are storable and provide level, strong and water-resistant coatings on the above materials.

PREPARATORY EXAMPLES (A) Compounds of the formula I

EXAMPLE 1

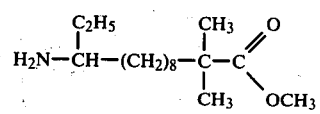

(a) With stirring, 975 g (4.37 moles) of 3,3-dimethyl-12-ethyl-1-azacyclododecene (prepared in accordance with Example β) are added dropwise in the course of about 35 minutes to a solution of 450 g (4.6 moles) of sulfuric acid in 600 g of water. The clear, slightly yellowish solution is then treated with steam for 20 minutes in order to remove any aldehyde impurities. The aqueous solution is subsequently stirred in an autoclave for 3 hours at 50° C. under an oxygen pressure of 20 bar. The acid reaction mixture is neutralised with sodium hydroxide solution, affording 820 g (3.2 moles) of 2,2-dimethyl-11-ethyl-11-aminoundecanoic acid, corresponding to a yield of 73% of theory. Melting point: 164°–165° C.

Analysis for $C_{15}H_{31}NO_2$ (molecular weight: 257.42): calculated: C 69.99%, H 12.14%, N 5.44%, O 12.43%; found: C 70.03%, H 12.10%, N 5.54%.

MS spectrum: molecular peak 257, fragment masses 228, 182, 140, 58.

(b) 51.4 g (0.2 mole) of 2,2-dimethyl-11-ethyl-aminoundecanoic acid and 200 ml of methanol and 22 g (0.224 mole) of sulfuric acid are refluxed for 3 hours.

Excess methanol is then distilled off, the residue is diluted with about 200 ml of water and the reaction solution is made weakly alkaline (pH 8–10) with aqueous sodium hydroxide, whereupon the amino acid ester separates as upper organic phase. Subsequent distillation yields 48.5 g (0.179 mole) of 2,2-dimethyl-11-ethyl-11-aminoundecanoic acid methyl ester, corresponding to a yield of 89.5% of theory.

b.p. 78°–80° C./0.05 torr, $n_D^{20} = 1.4494$.

Analysis for $C_{16}H_{33}NO_2$ (mol. wt. 271.45): calculated: C 70.80%, H 12.25%, N 5.16%, O 11.79%; found: C 70.54%, H 12.13%, N 5.10%, O 11.70%.

MS spectrum: molecular peak 271, fragment masses 242, 212, 182, 102, 58.

$^1$H-NMR spectrum τ (ppm): 6.43(s), 7.48(m), 8.75(s), 8.89(s) and 8.93(s) 9,13(t) in the ratio 3:1:18:8:3.

IR spectrum (liquid): ν (C=O)-1745 cm$^{-1}$.

EXAMPLE 2

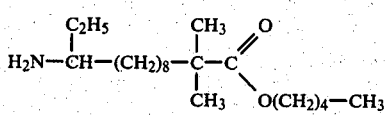

The procedure described in Example (1b) is repeated, using 200 ml of pentanol instead of 200 ml of methanol. Distillation yields 60.5 g (0.185 mole) of 2,2-dimethyl-11-ethyl-11-aminoundecanoic acid pentyl ester, corresponding to a yield of 92.5%.

b.p. 126°–128° C./0.02 torr; $n_D^{20} = 1.4494$.

Analysis for $C_{20}H_{41}NO_2$ (mol. wt. 327): calculated: C 73.40%, H 12.55%, N 4.28%, O 9.78%; found: C 73.43%, H 12.55%, N 4.51%, O 9.77%.

MS spectrum: molecular peak 327, fragment masses 298, 240, 212, 182, 170.

$^1$H-NMR spectrum τ (ppm): 5.96(t), 7.38(m), 8.2–8.7(m) and 8.80(s), 9.05(t) in the ratio 2:1:35:3.

IR spectrum (liquid): ν (C=O)-1750 cm$^{-1}$.

EXAMPLE 3

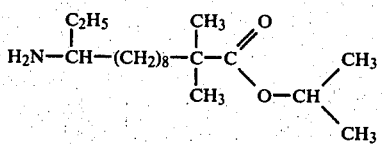

The procedure described in Example (1b) is repeated with the following modifications: 150 ml of isopropanol are used instead of 200 ml of methanol and an excess of gaseous HCl is used instead of 22 g (0.224 mole) of sulfuric acid. After a reaction time of 8 hours at reflux temperature, subsequent distillation yields 42 g (0.141 mole) of 2,2-dimethyl-11-ethyl-11-aminoundecanoic acid isopropyl ester, corresponding to a yield of 70.5%.

b.p. 95° C./0.01 torr; $n_D^{20} = 1.4469$.

Analysis for $C_{18}H_{37}NO_2$ (mol. wt. 299.50): calculated: C 72.19%, H 12.45%, N 4.68%, O 10.68%; found: C 72.12%, H 12.86%, N 4.96%, O 9.34%.

MS spectrum: molecular peak 299, fragment masses 270, 240, 212, 182, 170, 69.

$^1$H-NMR spectrum τ (ppm): 5.06(sept), 7.4(m), 8.4–8.75(m) and 8.80(s) and 8.85(s), 9.08(t) in the ratio 1:1:32:3.

IR spectrum (liquid): ν (C=O)-1745 cm$^{-1}$.

EXAMPLE 4

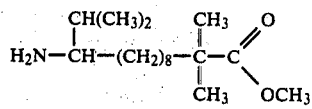

(a) The procedure described in Example (1a) is repeated, using 500 g (2.11 mole) of 3,3-dimethyl-12-isopropyl-1-azacyclododecene [prepared according to Example (α)], 250 g (2.55 mole) of sulfuric acid and 1 kg of water. After a reaction time of 6 hours at 50° C. under an oxygen pressure of 5 bar there are obtained 542 g (2 moles) of 2,2-dimethyl-11-isopropyl-11-aminoundecanoic acid, corresponding to a yield of 94.7% of theory. Melting point: 156°–159° C.

Analysis for $C_{16}H_{33}NO_2$ (mol. wt. 271.45): calculated: C 70.80%, H 12.25%, N 5.16%, O 11.79%; found: C 70.86%, H 12.43%, N 5.16%, O 11.66%.

MS spectrum: molecular peak 271, fragment masses 256, 228, 140, 72.

(b) The procedure described in Example (1b) is repeated, using 54.2 g (0.2 mole) of 2,2-dimethyl-11-isopropyl-11-aminoundecanoic acid. Distillation yields 51 g (0.179 mole) of 2,2-dimethyl-11-isopropyl-11-aminoundecanoic acid methyl ester, corresponding to a yield of 89.5% of theory.

b.p. 106°–107° C./0.03 torr; $n_D^{20} = 1.4511$.

Analysis for $C_{17}H_{35}NO_2$ (mol. wt. 285.47): calculated: C 71.53%, H 12.36%, N 4.91%, O 11.21%; found: C 71.69%, H 12.52%, N 4.99%, O 11.23%.

MS spectrum: molecular peak 285, fragment masses 270, 254, 285, 182, 140, 102, 72.

$^1$H-NMR spectrum τ (ppm): 6.33(s), 7.5(m), 8.2–8.7(m), 8.82(s), 8.97(s), 9.12(dd) in the ratio 3:1:17:6:2:6.

IR spectrum (liquid): ν (C=O)-1745 cm$^{-1}$.

EXAMPLE 5

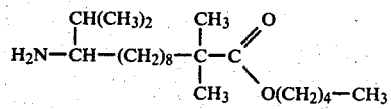

The procedure described in Example (1b) is repeated, using 52.3 g (0.193 mole) of 2,2-dimethyl-11-aminoundecanoic acid and 200 ml of n-pentanol. Distillation yields 60.5 g (0.178 mole) of 2,2-dimethyl-11-isopropyl-11-aminoundecanoic acid pentyl ester, corresponding to a yield of 92.2% of theory: b.p. 138°–139°/0.01 torr; $n_D^{20} = 1.4505$.

Analysis for $C_{21}H_{43}NO_2$ (mol. wt. 341): calculated: C 73.80%, H 12.65%, N 4.10%, O 9.38%; found: C 73.99%, H 12.77%, N 4.16%, O 9.36%.

MS spectrum: molecular peak 341, fragment masses 298, 254, 226, 182, 140, 72.

$^1$H-NMR spectrum τ (ppm): 5.98(t), 7.5(m), 8.3–8.7(m), 8.80(s), 8.89(s), 9.09(dt) in the ratio 2:1:26:6:2:6.

IR spectrum (liquid): ν (C=O)-1750 cm$^{-1}$.

EXAMPLE 6

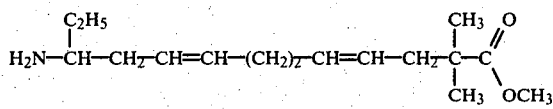

The procedure described in Example (1a) is repeated, using 55 g (0.251 mole) of 3,3-dimethyl-12-ethyl-1-aza-1,5,9-cyclododecatriene, 27 g (0.275 mole) of sulfuric acid and 500 g of water. The oily amino acid obtained is then immediately further reacted, as described in Example (1b), in the presence of 100 ml of methanol. Subsequent distillation yields 10.5 g (0.0394 mole) of 2,2-dimethyl-11-ethyl-11-aminoundeca-4,8-dienoic acid methyl ester, corresponding to a yield of 15.7% of theory;

b.p. 106°-108° C./0.3 bar; $n_D^{20} = 1.4754$.

Analysis for $C_{16}H_{29}NO_2$ (mol. wt. 267.41): calculated: C 71.87%, H 10.93%, N 5.24%, O 11.97%; found: C 71.55%, H 10.93%, N 5.64%, O 11.94%.

MS spectrum: molecular peak 267, fragment masses 238, 236, 208, 166, 140, 95.

$^1$H-NMR spectrum τ (ppm): 4.6(m), 6.36(s), 7.35(m), 7.7-8.0(m), 8.4(s) and 8.57(m), 8.82(s), 9.06(t) in the ratio 4:3:1:8:4:6:3.

EXAMPLE 7

The procedure described in Example (1b) is repeated, using 50 g (0.185 mole) of 2,2-dimethyl-11-isopropyl-11-aminoundecanoic acid and 100 ml of isopropanol. Distillation yields 44 g (0.141 mole) of 2,2-dimethyl-11-isopropyl-11-aminoundecanoic acid isopropyl ester, corresponding to a yield of 76% of theory;

b.p. 118°-120° C./0.03 torr; $n_D^{20} = 1.4481$.

Analysis for $C_{19}H_{39}NO_2$ (mol. wt. 313.53): calculated: C 72.79%, H 12.54%, N 4.47%, O 10.21%; found: C 72.46%, H 12.69%, N 4.71%, O 9.56%.

MS spectrum: molecular peak 313, fragment masses 298, 270, 254, 226, 182, 72.

EXAMPLE β

The procedure of Example (α) is repeated, using 438 g (2 moles) of 3,3-dimethyl-12-ethyl-1-aza-1,5,9-cyclododecatriene. Distillation yields 412 g (1.85 moles) of 3,3-dimethyl-12-ethyl-1-aza-cyclododecene; b.p. 61°-63° C./4 Pa; $n_D^{20} = 1.4721$.

EXAMPLE γ

The procedure described in Example (α) is repeated, using 253.4 g (1 mole) of 3-methyl-12-phenyl-1-aza-1,5,9-cyclododecatriene. Distillation yields 243 g (0.945 mole) of 3-methyl-12-phenyl-1-azacyclododecene; b.p. 110°-112° C./0.03 torr.

EXAMPLE 8

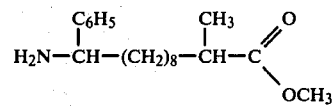

The procedure described in Example (1a) is repeated, using 65 g (0.253 mole) of 3-methyl-12-phenyl-1-aza-cyclododecene. After the oxidation, without isolation of the amino acid, the procedure of Example (1b) is repeated using 500 ml of methanol. Subsequent distillation yields 27 g (0.0885 mole) of 2-methyl-11-phenyl-11-aminoundecanoic acid methyl ester, corresponding to a yield of 35% of theory; b.p. 135° C./0.02 torr; $n_D^{20} = 1.5000$.

Analysis for $C_{19}H_{31}NO_2$ (mol. wt. 305.46): calculated: C 74.71%, H 10.23%, N 4.58%, O 10.47%; found: C 75.43%, H 10.62%, N 4.68%, O 9.90%.

MS spektrum: molecular peak 305, fragment masses 274, 200, 106.

$^1$H-NMR spectrum τ (ppm): 2.71(s), 6.14(t), 6.36(s), 7.6(m), 8.2-8.75(m) and 8.84(d) in the ratio 5:1:3:1:18:3.

USE EXAMPLES

EXAMPLE I

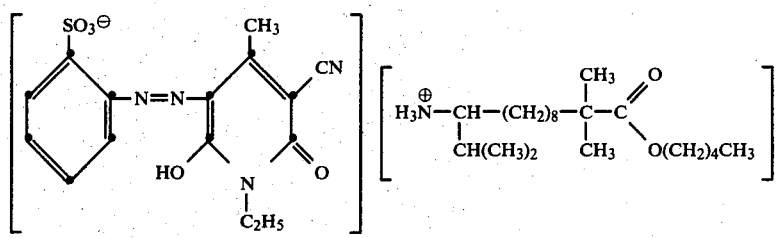

$^1$H-NMR spectrum τ (ppm): 5.05(sep), 7.5(m), 8.2-9.0(m) and 9.1(d) in the ratio 1:1:31:6.

(B) Compounds of the formula II

EXAMPLE α

466.8 g (2 moles) of 3,3-dimethyl-12-isopropyl-1-aza-1,5,9-cyclododecatriene are dissolved in 4 liters of cyclohexane and the solution is hydrogenated in a steel autoclave for 4 hours at 20°-25° C. under an initial pressure of 100 bar in the presence of 50 g of rhodium-/aluminium oxide. The solvent is removed by distillation and the main fraction consists of 425 g (1.79 L mole) of 3,3-dimethyl-12-isopropyl-1-aza-cyclododecene; b.p. 92°-94° C./4 Pa; $n_D^{20} = 1.4706$.

19.2 g (0.05 mole) of the sodium salt of the monoazo dye obtained by coupling 2-aminobenzenesulfonic acid to 1-ethyl-2-hydroxy-4-methyl-5-cyano-pyridone-6 are suspended in 500 ml of water. A mixture of 17.1 g (0.05 mole) of 2,2-dimethyl-11-isopropyl-11-aminoundecanoic acid pentyl ester (see Example 5), 4 ml of 85% formic acid and 80 ml of water is then added dropwise. The suspension is stirred for several hours at 45°-50° C., and filtered. The filter cake is washed first with dilute formic acid, then with water, and dried in vacuo at 60° C., affording 35.7 g of the solvent dye of the above formula. The dye is very readily soluble in ethanol, acetone, ethyl acetate and ethylene glycol monoethyl ether.

Valuable yellow solvent dyes are likewise obtained by an analogous procedure using the equimolar amount of one of the amines obtained according to Examples 1 to 4 and 6 to 8 instead of 0.05 mole of 2,2-dimethyl-11-isopropyl-11-aminoundecanoic acid pentyl ester.

EXAMPLE II 48.6 g (0.1 mole) of the sodium salt of the monoazo dye obtained by coupling aniline-2,4-disulfonic acid to 1-ethyl-2-hydroxy-4-methyl-5-cyano-pyridine-5 are stirred in 300 ml of water and 300 ml of methyl isobutyl ketone. Then 68.4 g (0.2 mole) of 2,2-dimethyl-11-isopropyl-11-aminoundecanoic acid pentyl ester and formic acid are added to the above mixture dropwise until a pH value of 3.5-4 is attained. The reaction mixture is stirred for 1 hour at 40°-45° C., both phases are separated and the organic phase is washed with 250 ml of water. The solvent is distilled off and the residue is dried in vacuo at elevated temperature, affording 88 g of yellow dye salt which is very readily soluble in the solvents customarily employed in the printing ink and lacquer sector, for example in acetone, methanol, ethanol, isopropanol, n-butanol, benzyl alcohol, ethylene glycol monomethyl and monoethyl ether, and in solvent mixtures, such as ethanol/toluene (70:30), ethanol/ethylene glycol monoethyl ether (85:15), ethanol/ethyl acetate (50:50), methylene chloride/methanol (9:1). The printing inks, coloured lacquers and acetate fibres obtained therewith are distinguished by a pure, yellow shade.

EXAMPLE III 5 g of the dye salt obtained in Example I are added to 95 g of a nitrocellulose lacquer obtained from 15 g of alcohol-soluble, low viscosity nitrocellulose with about 18% of dibutyl phthalate, 10 g of ethylene glycol monoethyl ether, 20 g of ethyl acetate and 50 g of 94% ethanol. The mixture is stirred until the colourant is evenly distributed. The lacquer is then applied with a film applicator (handcoater of RK Chemical CO. Ltd., Royston, England) to a wet film thickness of about 12 μm to opaline paper or an aluminium lined foil and dried, producing a firmly adhering, uniform, strong yellow finish which has excellent resistance to exposure and to treatment with water and butter.

COMPARISON EXAMPLE IV

The procedure of Example I is repeated using 12.2 g (0.05 mole) of 11-aminoundecanoic acid isopropyl ester. The resultant product (29.8 g) is a yellow dye which is only very sparingly soluble in the commonly employed solvents. In contrast to the dye salts of branched aminoundecanoates, it cannot be used as a solvent dye.

What is claimed is:

1. A compound of the formula I

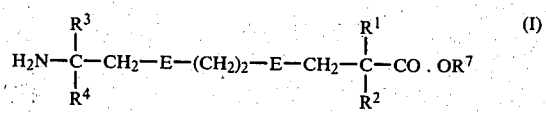

wherein each of $R^1$ and $R^3$ independently is hydrogen or a straight chain or branched alkyl radical of 1 to 8 carbon atoms, and $R^3$ is also a phenyl radical, $R^2$ is a straight chain or branched alkyl radical of 1 to 8 carbon atoms and $R^4$ is a straight chain or branched alkyl radical of 1 to 18 carbon atoms, or $R^1$ and $R^2$ $R^3$ and $R^4$ or both pairs together with the carbon atom to which they are individually attached each form a cycloaliphatic ring containing 4 to 8 carbon atoms, and wherein each E represents one of the radicals

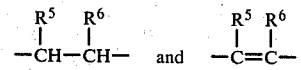

in which each of $R^5$ and $R^6$ independently is hydrogen or alkyl of 1 to 4 carbon atoms and $R^7$ is hydrogen or a straight chain or branched alkyl radical containing altogether 1 to 18 carbon atoms.

2. An 11-aminoundecanoic acid according to claim 1, wherein $R^7$ in formula I is hydrogen and E is the radical

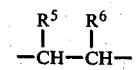

3. An 11-aminoundecanoic acid ester according to claim 1, wherein $R^7$ in formula I is a straight chain or branched alkyl radical containing altogether 1 to 18 carbon atoms, and E is the radical

4. An 11-aminoundeca-4,8-dienoic acid ester according to claim 1, wherein $R^7$ in formula I is a straight chain or branched alkyl radical containing altogether 1 to 18 carbon atoms, and E is the radical

5. A compound of the formula I according to claim 1, wherein each of $R^5$ and $R^6$ is hydrogen, each of $R^1$ and $R^3$ independently is hydrogen or alkyl of 1 to 5 carbon atoms, $R^2$ is alkyl of 1 to 5 carbon atoms and $R^4$ is alkyl of 1 to 7 carbon atoms, or wherein each of $R^3$, $R^5$ and $R^6$ is hydrogen, $R^1$ and $R^2$ together with the carbon atoms to which they are attached are cyclopentyl or cyclohexyl, and $R^4$ is alkyl of 1 to 7 carbon atoms.

6. A compound of the formula I according to claim 1, wherein each of $R^3$, $R^5$ and $R^6$ is hydrogen, each of $R^1$ and $R^2$ independently is alkyl of 1 to 4 carbon atoms or together with the carbon atom to which they are attached are cyclohexyl, and $R^4$ is alkyl of 1 to 7 carbon atoms.

7. A compound of the formula I according to claim 1, wherein $R^3$ is hydrogen and $R^4$ is the radical of the formula

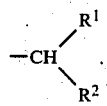

8. A compound of the formula I according to claim 1, wherein each of $R^1$ and $R^2$ is $—CH_3$, $R^4$ is $—CH(CH_3)_2$, E is $—CH_2CH_2$ and $R^7$ is n-pentyl.

* * * * *